(12) United States Patent
Fann et al.

(10) Patent No.: US 7,754,247 B2
(45) Date of Patent: Jul. 13, 2010

(54) RESUSCITATION FLUID

(75) Inventors: Stephan Fann, Columbia, SC (US);
Michael J. Yost, Lexington, SC (US)

(73) Assignee: University of South Carolina

( * ) Notice: Subject to any disclaimer, the term of this patent is extended or adjusted under 35 U.S.C. 154(b) by 0 days.

(21) Appl. No.: 11/807,409

(22) Filed: May 29, 2007

(65) Prior Publication Data
US 2008/0299224 A1 Dec. 4, 2008

(51) Int. Cl.
*A61K 33/14* (2006.01)
*A01N 59/08* (2006.01)

(52) U.S. Cl. .................................... 424/680

(58) Field of Classification Search ................. 424/680
See application file for complete search history.

(56) References Cited

U.S. PATENT DOCUMENTS

| | | | |
|---|---|---|---|
| 5,100,677 A | 3/1992 | Veech | 424/677 |
| 5,602,183 A * | 2/1997 | Martin et al. | 514/724 |
| 6,391,332 B1 * | 5/2002 | Somerville et al. | 424/439 |
| 6,943,190 B2 * | 9/2005 | Fink et al. | 514/456 |
| 2005/0215468 A1 | 9/2005 | Bar-Or et al. | |
| 2006/0034941 A1 * | 2/2006 | Dobson | 424/608 |

FOREIGN PATENT DOCUMENTS

WO WO2008011670 1/2008

OTHER PUBLICATIONS

K. Modelska, et al., *Inhibition of β-adrenergic-dependent alveolar epithelial clearance by oxidant mechanisms after hemorrhagic shock*, The American Physiological Society, Alveolar Fluid Clearance and Oxidative Epithelial Injury, pp. L844-L857, Received Aug. 20, 1998; accepted in final form Jan. 27, 1999.

Jie Fan, et al., *Hemorrhagic Shock Primes for Increased Expression of Cytokine-Induced Neutrophil Chemoattractant in the Lung: Role in Pulmonary Inflammation Following Lipopolysaccharide*, The American Association of Immunologists, The Journal of Immunology 0022-1767/98, pp. 440-447.

Pedro Cabrales, et al. *Hemorrhagic shock resuscitation with carbon monoxide saturated blood*, Elsevier Experimental Paper, Tissue injury after resuscitation, Received May 2, 2006; received in revised form Jun. 7, 2006; accepted Jun. 7, 2006, Resuscitation (2007) 72, pp. 306-318, www.elsevier.com/locate/resuscitation © 2006 Elsevier Ireland Ltd.

Frederick A. Moore, MD, et al., *Inflammation and the Host Response to Injury, a Large-Scale Collaborative Project: Patient-Oriented Research Core-Standard Operating Procedures for Clinical Care*, III. Guidelines for Shock Resuscitation, J Trauma, 2006;61:82-89.

Paulo Nascimento, Jr., M.D., Ph.D., et al., *Early Hemodynamic and Renal Effects of Hemorrhagic Shock Resuscitation with Lactated Ringer's Solution, Hydroxyethyl Starch, and Hypertonic Saline with or without 6% Dextran-70*, Journal of Surgical Research 136, 98-105 (2006).

Raul Coimbra, MD, PhD, FACS, et al., *HSPTX Protects Against Hemorrhagic Shock Resuscitation-Induced Tissue Injury: An Attractive Alternative to Ringer's Lactate*, The Journal of Trauma®, Injury, Infection, and Critical Care, vol. 60 • No. 1, pp. 41-51. Submitted for publication Sep. 28, 2005. Accepted for Publication Nov. 11, 2005.

Andrew B. Cooper, et al., *Five percent albumin for adult burn shock resuscitation: lack of effect on daily multiple organ dysfunction score*, Transfusion Practice, vol. 46, Jan. 2006, pp. 80-89.

Michael L. Cheatham, MD, FCCM, *The Holy Grail of shock resuscitation**, Crit Care Med 2005 vol. 33, No. 11, pp. 2691-2692.

Pedro Cabrales, et al., *Early Difference in Tissue pH and Microvascular hemodynamics in Hemorrhagic Shock Resuscitation Using Polyethylene Glycol-Albumin- and Hydroxyethyl Starch-Based Plasma Expanders*, Shock, vol. 24, No. 1, pp. 66-73, 2005. Received Feb. 2, 2005; first review completed Feb. 22, 2005; accepted in final form Apr. 2, 2005.

Guillaume Savoye, et al., *Hemorrhagic Shock Resuscitation Affects Early and Selective Mesenteric Artery Endothelial Function Through a Free Radical-Dependent Mechanism*, Shock, vol. 23, No. 5, pp. 411-416, 2005. Received Aug. 11, 2004; first review completed Sep. 8, 2004; accepted in final form Feb. 8, 2005.

G. Tom Shires, MD, et al., *The effect of shock resuscitation fluids on apoptosis*, Excerpta Medica, The American Journal of Surgery 1989 (2005) 85-91, Rapid communication. Manuscript received May 3, 2004; revised manuscript Jun. 23, 2004.

(Continued)

*Primary Examiner*—Johann R Richter
*Assistant Examiner*—Luke E Karpinski
(74) *Attorney, Agent, or Firm*—Dority & Manning, P.A.

(57) ABSTRACT

The present invention relates to a resuscitation fluid which includes an ionic salt at a concentration above about 0.9%, at least one soluble protein, at least one intermediate energy substrate, and optionally an agent to mitigate intracellular acidosis. Methods of making and using the fluid are also described.

42 Claims, No Drawings

OTHER PUBLICATIONS

C. Holm, et al., *A clinical randomized study on the effects of invasive monitoring on burn shock resuscitation*, Burns 30 (2004) 798-807. Accepted Jun. 2, 2004. www.elsevier.com/locate/burns.

José Reinaldo Cerqueira Braz, MD, PhD, et al., *The Early Systemic and Gastrointestinal Oxygenation Effects of Hemorrhagic Shock Resuscitation with Hypertonic Saline and Hypertonic Saline 6% Dextran-70: A Comparative Study in Dogs*, Anesth Analg 2004; 99:536-46. International Anesthesia Research Society.

Frederick A. Moore, et al., Trauma III, *The next generation in shock resuscitation*, Lancet 2004; 363:1988-96. The Lancet • vol. 363 • Jun. 12, 2004 • www.thelancet.com pp. 1988-1996.

Alan B. Marr, et al., *Preload Optimization Using "Starling Curve" Generation During Shock Resuscitation: Can It Be Done?*, Shock, vol. 21, No. 4, pp. 300-305, 2004. Received Sep. 8, 2003; first review completed Oct. 14, 2003; accepted in final form Dec. 19, 2003.

El Rasheid Zakaria, et al., *Role of Neutrophils On Shock/Resuscitation-Mediated Intestinal Arteriolar Derangements*, Shock, vol. 21, No. 3, pp. 248-253, 2004. Received Sep. 19, 2003; first review completed Oct. 14, 2003; accepted in final form Nov. 10, 2003.

Kinga A. Powers, MD, et al., *Twenty-five percent albumin prevents lung injury following shock/resuscitation*, Crit Care Med 2003 vol. 31, No. 9, pp. 2355-2363.

Ori D. Rotstein, MD, *Modeling the Two-Hit Hypothesis for Evaluating Strategies to Prevent Organ Injury after Shock/Resuscitation*, J. Trauma 2003;54:S203-S206. The Journal of Trauma® Injury, Infection, and Critical Care, vol. 54 • No. 5, May Supplement 2003.

José L. Pascual, et al., *Hemorrhagic Shock Resuscitation with a Low Molecular Weight Starch Reduces Neutrophil-Endothelial Interactions and Vessel Leakage* in vivo, Surgical Infections, vol. 2, No. 4, 2001 © Mary Ann Liebert, Inc., pp. 275-288.

Zsolt Balogh, MD, et al., *Secondary abdominal compartment syndrome is an elusive early complication of traumatic shock resuscitation*, Excerpta Medica, The American Journal of Surgery 184 (2002) 538-544, Scientific paper. Manuscript received Jul. 31, 2002; revised manuscript Aug. 18, 2002. Presented at the 54th Annual Meeting of the Southwestern Surgical Congress, Coronado, California, Apr. 7-10, 2002.

Kinga A. Powers, MD, et al., *25% albumin modulates adhesive interactions between neutrophils and the endothelium following shock/resuscitation*, Surgery, Aug. 2002, pp. 391-398.

Yasuhiko Yamakawa, PhD, *Interaction of Platelet Activating Factor, Reactive Oxygen Species Generated by Xanthine Oxidase, and Leukocytes in the Generation of Hepatic Injury After Shock/Resuscitation*, Annals of Surgery, vol. 231, No. 3, 387-398, Mar. 2000 © 2000 Lippincott Williams & Wilkins, Inc.

Takuro Saito, et al., *The Differential Induction of Two Immediate Early Genes, c-fos and c-jun, After Systemic Hypovolemic Shock/Resuscitation in the Rat Liver and Kidney*, Surg Today Jpn J Surg (1998) 28:608-617. Surgery Today © Springer-Verlag 1998. Received for publication on Nov. 19, 1996; accepted on Jul. 8, 1997.

Michael T. Handrigan, et al., *Hydroxyethyl Starch Inhibits Neutrophil Adhesion and Transendothelial Migration*, Shock, vol. 24, No. 5, pp. 434-439, 2005. Received Apr. 20, 2005; first review completed May 11, 2005; accepted in final form Jun. 24, 2005.

Aaron M. Cheng, M.D., et al., *Polymerized Hemoglobin Induces Heme Oxygenase-1 Protein Expression and Inhibits Intercellular Adhesion Molecule-1 Protein Expression in Human Lung Microvascular Endothelial Cells*, J. Am Coll Surg, pp. 579-584. Received Mar. 25, 2005; Revised May 9, 2005; Accepted May 11, 2005. © 2005 by the American College of Surgeons.

Henry M. Cryer, M.D., Ph.D., et al., *The effect of hypertonic saline resuscitation on responses to severe hemorrhagic shock by the skeletal muscle, intestinal, and renal microcirculation systems: seeing is believing*, Excerpta Medica, The American Journal of Surgery 190 (2005) 305-313, Scientific paper. Manuscript received Apr. 13, 2005; accepted revised manuscript Apr. 15, 2005.

Michael T. Handrigan, et al., *Choice of Fluid Influences Outcome in Prolonged Hypotensive Resuscitation After Hemorrhage in Awake Rats*, Shock, vol. 23, No. 4, pp. 337-343, 2005. Received Nov. 9, 2004; first review completed Nov. 24, 2004; accepted in final form Jan. 5, 2005.

Vadim Gushchin, M.D., et al., *cDNA Profiling in Leukocytes Exposed to Hypertonic Resuscitation Fluids*, J AM Coll Surg 2003;197:426-432. © 2003 by the American College of Surgeons. Received Jan. 30, 2003; Revised Mar. 27, 2003; Accepted Apr. 8, 2003.

Wilfred Lieberthal, et al., *Comparison of the Effects of a 50% Exchange-Transfusion With Albumin, Hetastarch, and Modified Hemoglobin Solutions*, Shock, vol. 17, No. 1, pp. 61-69, 2002. Received Jan. 3, 2001; first review completed Jan 23, 2001; accepted in final form Apr. 6, 2001.

MariaElaina Sumas, M.D., et al., *Tonicity of Resuscitative Fluids Outcome after Spinal Cord Injury*, Experimental Studies, Neurosurgery, vol. 48, No. 1, Jan. 2001, pp. 167-173.

Michelle C. Mazzoni, et al., *Dynamic fluid redistribution in hyperosmotic resuscitation of hypovolemic hemorrhage*, pp. H629-H637, Copyright © 1988 the American Physiological Society. Received Dec. 21, 1987; accepted in final form Apr. 21, 1988.

Donna M. Wilder, et al., *Hypertonic resuscitation and blood coagulation* In vitro *comparison of several hypertonic solutions for their action on platelets and plasma coagulation*, Regular Article, Pergamon, Thrombosis Research 107 (2002) 255-261. Accepted Oct. 22, 2002. © 2002 Elsevier Science Ltd.

Donna L. Dyess, et al., *Effects of hypertonic saline and Dextran 70 resuscitation on microvascular permeability after burn*, pp. H1832-H1837, Copyright © 1992 the American Physiological Society. Received May 23, 1991; accepted in final form Jan. 17, 1992.

Rainer Kentner, et al., *Titrated hypertonic/hyperoncotic solution for hypotensive fluid resuscitation during uncontrolled hemorrhagic shock in rats*, Elsevier Resuscitation 65 (2005) 87-95, Received Jan. 24, 2002; received in revised form Oct. 19, 2004; accepted Oct. 19, 2004, www.elsevier.com/locate/resuscitation © 2004 Elsevier Ireland Ltd.

Pedro Cabrales, et al., *Hyperosmotic-Hyperoncotic Versus Hyperosmotic-Hyperviscous: Small Volume Resuscitation in Hemorrhagic Shock*, Shock, vol. 22, No. 5, pp. 431-437, 2004. Received May 5, 2004; first review completed May 20, 2004; accepted in final form Jul. 16, 2004.

Osvaldo Chiara, MD, et al., *Resuscitation from hemorrhagic shock: Experimental model comparing normal saline, dextran, and hypertonic saline solutions*, Clinical Investigations, Crit Care Med 2003 vol. 31, No. 7, pp. 1915-1922. Copyright (2) 2003 by Lippincott Williams & Wilkins.

Paula F. Moon, et al., *Fluid compartments in hemorrhaged rats after hyperosmotic crystalloid and hyperoncotic colloid resuscitation*, Copyright © 1996 the American Physiological Society, pp. F1-F8. Received Dec. 22, 1994; accepted in final form May 15, 1995.

James W. Holcroft, M.D., et al., *3% NaCl and 7.5% NaCl/Dextran 70 in the Resuscitation of Severely Injured Patients*, Ann. Surg. • Sep. 1987, pp. 279-287.

Wilfred Lieberthal, et al., *Comparison of the Effects of a 50% Exchange-Transfusion With Albumin, Hetastarch, and Modified Hemoglobin Solutions*, Shock, vol. 17, No. 1, pp. 61-69, 2002. Received Jan. 3, 2001; first review completed Jan. 23, 2001; accepted in final form Apr. 6, 2001.

Robert L. Sheridan, et al., *Trends in blood conservation in burn care*, Burns 27 (2001) 272-276. Accepted May 23, 2000. www.elsevier.com/locate/burns.

Rinaldo Bellomo, MD, et al., *The effects of saline or albumin resuscitation on acid-base status and serum electrolytes*, Crit Care Med 2006 vol. 34, No. 12, pp. 2891-2897.

Lee-Wei Chen, MD, et al., *Inhibition of Nitric Oxide Synthase Reverses the Effect of Albumin on Lung Damage in Burn*, © 2005 by the American College of Surgeons, vol. 200, No. 4, Apr. 2005. Received Jul. 7, 2004; Revised Sep. 24, 2004; Accepted Nov. 2, 2004. Published by Elsevier Inc.

Charles E. Lucas, M.D., F.A.C.S., et al., *The Effects of Hespan on Serum and Lymphatic Albumin, Globulin, and Coagulant Protein*, Submitted for publication: Oct. 22, 1987. Ann. Surg. • Apr. 1988, vol. 207 • No. 4, pp. 416-420.

Walter C. Leibold, M.D., et al., *Effect of Albumin Resuscitation on Canine Coagulation Activity and Content*, Submitted for publication: Mar. 10, 1983. Ann. Surg. • Nov. 1983, vol. 198 • No. 5, pp. 630-633.

Charles E. Lucas, M.D., F.A.C.S., et al., *Altered Coagulation Protein Content After Albumin Resuscitation*, Submitted for publication Jan. 20, 1982. Ann. Surg. • Aug. 1982, vol. 196 • No. 2, pp. 198-202.

Tom Lin, MD, et al., *Energy Substrate-Supplemental Resuscitation Affects Brain Monocarboxylate Transporter Levels and Gliosis in a Rat Model of Hemorrhagic Shock*, J Trauma. 2005;59:1191-1202. The Journal of Trauma® Injury, Infection, and Critical Care, vol. 59 • No. 5, pp. 1191-1202. Submitted for publication Oct. 15, 2004. Accepted for publication Aug. 11, 2005. Copyright © 2005 by Lippincott Williams & Wilkins, Inc.

Richard Rokyta Jr., et al., *Effects of continuous venovenous haemofiltration-induced cooling on global haemodynamics, splanchnic oxygen and energy balance in critically ill patients*, Nephrol Dial Transplant (2004) 19: 623-630. Nephrology Dialysis Transplantation vol. 19 No. 3 © ERA-EDTA 2004.

Elena Koustova, PhD, et al., *Ketone and pyruvate Ringer's solutions decrease pulmonary apoptosis in a rat model of severe hemorrhagic shock and resuscitation*, Surgery 2003;134:267-74. Surgery, vol. 134, No. 2, Aug. 2003, pp. 267-274.

Tatsuo Fukuse, et al., *Influence of Deflated and Anaerobic Conditions During Cold Storage on Rat Lungs*, Am J Respir Crit Care Med 1999, vol. 160. pp. 621-627. Received in original form Sep. 9, 1998 and in revised form Jan. 20, 1999.

PCT International Search Report, PCT/US2008/06723, International Filing Date May 28, 2008.

* cited by examiner

RESUSCITATION FLUID

BACKGROUND OF THE INVENTION

The present invention relates generally to the treatment and prevention of hemorrhagic and ischemia disorders. More specifically, the present invention relates to a method and composition for treating and preventing one or more of hemorrhagic shock, septic shock, hypotension, acidosis, and/or hypovolemia.

Shock is a serious medical condition where the rate of tissue perfusion is insufficient to meet demand for oxygen and nutrients. This hypoperfusion state is a life-threatening medical emergency and one of the leading causes of death for critically ill people. Shock may also lead to many other medical emergencies, such as hypoxia and/or cardiac arrest.

The management of shock requires immediate intervention. Re-establishing perfusion to the organs is the primary goal and is achieved by restoring and maintaining the blood circulating volume, ensuring oxygenation and blood pressure are adequate, achieving and maintaining effective cardiac function, and preventing complications.

The prognosis of shock depends on the underlying cause and the nature and extent of concurrent problems. Hypovolemic, anaphylactic, and neurogenic shock are readily treatable and respond well to medical therapy. Septic shock, however, is a grave condition with a mortality rate between 30% and 50%. The prognosis of cardiogenic shock is even worse.

Shock is said to evolve from reversible to irreversible in experimental hemorrhagic shock involving certain animal species (dogs, rats, mice) that develop intense vasoconstriction of the gut. Death is due to hemorrhagic necrosis of the intestinal lining when shed blood is reinfused. In pigs and humans, this is not seen and cessation of bleeding and restoration of blood volume is usually very effective. Prolonged hypovolemia and hypotension does, however, carry a risk of respiratory and then cardiac arrest. Insufficient perfusion of the brain may be the greatest danger during shock. Urgent treatment is essential for a good prognosis in hypovolemic shock.

Shock, at its most fundamental, can be considered a warm ischemia. Warm ischemia is an absolute or relative shortage of the blood supply to an organ or tissues. Ischemia can also be described as an inadequate flow of blood to a part of the body, caused by constriction or blockage of the blood vessels supplying it. Since oxygen is mainly bound to hemoglobin in red blood cells, insufficient blood supply causes tissue to become hypoxic, or, if no oxygen is supplied at all, anoxic. This can cause necrosis (i.e., cell death). Necrosis due to ischemia usually takes about 3-4 hours.

Tissues that are especially sensitive to inadequate blood supply include the heart, the kidneys, and the brain. Ischemia in brain tissue, for example due to stroke or head injury, causes a process called the ischemic cascade to be unleashed, in which proteolytic enzymes, reactive oxygen species, and other chemicals that are harmful in this context can damage and may ultimately kill brain tissue. Restoration of blood flow after a period of ischemia can actually be more damaging than the ischemia. Reintroduction of oxygen causes a greater production of damaging free radicals, resulting in reperfusion injury. With reperfusion injury, necrosis can be greatly accelerated.

The present standard of care in the initial management of shock includes rapid administration of large volumes of isotonic crystalloid solution, which can be up to several liters in an adult patient. In situations where fluid addition to the vascular system is required, such as for resuscitation, the practice has been to add isotonic fluids in sufficient quantity to replenish vascular fluid volume. In practice, this has often been at a rate of 1:1 as compared to blood loss, and often as high as 3:1 compared to blood loss due to physiologic equilibration of resuscitative fluid between the intravascular and interstitial space. Advantages of this practice were avoidance or reduction in triggering anti-inflammatory response, the provision of oxygen to the cells, and the replenishment of osmotic pressure in the vascular system. On the other hand, large volumes of fluids are required to be administered, and cell death often occurs despite the additions of large volumes of the fluids due to cells lapsing into a regime of anaerobic metabolism from which they could not recover.

A preferred fluid is Ringer's lactate, although normal saline or other similar isotonic crystalloid solutions are also used. Recommended continued treatment is based on the observed response to the initial fluid therapy. *American College of Surgeons,* 154, 585-588, (1987). As a general rule, guidelines are based on the "three for one" rule. This is based on the long-standing empirical observation that most hemorrhagic shock patients require up to 300 mL of electrolyte solution for each 100 mL of blood lost.

Other isotonic fluid replacement solutions have been used, including isotonic crystalloid solutions mixed with macromolecular solutions of plasma proteins or synthesized molecules with similar oncotic properties (colloids); including albumin, dextran, hetastarch or polygelatin in 0.9% NaCl. Whole blood is also used, but it is expensive, often unavailable and cross matching may delay therapy.

Crystalloids and colloids have been used as volume expanders, but generally must be infused in large volume. Such large volumes may cause peripheral and pulmonary edema. Additionally, the large volume requirements of isotonic fluids means that there are time delays and logistic difficulties associated with vascular delivery of effective therapy.

Hyperosmotic crystalloid and hyperosmotic/hyperoncotic (crystalloid/colloid) formulations have been reported to offer some physiological benefits for the treatment of circulatory shock, including improved efficacy for restoration of overall cardiovascular function in animals and man compared to conventional resuscitation. U.S. Pat. No. 3,993,750. Normalization of circulatory function has been obtained with such solutions. U.S. Pat. No. 4,927,806. Small volumes of salt/concentrated dextran formulations have been shown to rapidly restore and sustain normalization of circulatory function in hemorrhage. Surgery 100, 239-246 (1986) and U.S. Pat. No. 4,908,350. However, there remain some important limitations/side effects.

Hypertonic saline infusions in shocked animals and patients have been shown to cause an initial acidosis and hypokalemia. Treatment with hypertonic saline can also lead to a hyperchloremic acidosis, possibly due to excessive chloride load. Some isotonic Ringers solutions and mildly hypertonic formulations mimic sodium and chloride concentration ratios found in plasma and are thought to decrease the likelihood of acidosis. U.S. Pat. No. 3,993,750. Circulatory shock is often associated with an acidosis and, therefore, increased acidotic insult may be deleterious.

Although hypertonic saline rapidly improves both blood pressure and cardiac output, these beneficial effects may be overshadowed by deleterious effects from increased blood pressure. Uncontrolled internal bleeding in trauma patients may be aggravated by increased pressure, leading to increased bleeding. Return of normal blood pressure resulting in increased bleeding due to arterial pressure increase may lead to increased mortality over no treatment. Therefore, ideal pre-hospital resuscitation would increase cardiac output but only modestly increase blood pressure.

Another aspect of resuscitation fluids is their use under less than ideal (non-hospital) conditions. Logistic restraints may severely curtail transportation of weighty or voluminous material. In battlefield situations it may be impractical to administer large volumes, yet there is a critical need to rapidly restore oxygen delivery to critical organs and to prevent or reverse the effects of traumatic shock.

SUMMARY OF THE INVENTION

Briefly, therefore, the present invention is directed to a resuscitation fluid comprising: an ionic salt at a concentration over about 0.9% by weight; at least one soluble protein; an intermediate energy substrate; and optionally an agent to mitigate intracellular acidosis.

The present invention is also directed to a method of preventing or treating septic shock, hemorrhagic shock, hypotension, acidosis, and/or hypovolemia, the method comprising: administering to a subject in need of treatment or prevention of one or more of septic shock, hemorrhagic shock, hypotension, acidosis, and/or hypovolemia at least one ionic salt, at least one soluble protein, and at least one intermediate energy substrate.

The present invention is also directed to a method of making a resuscitation fluid, the method comprising intermixing at least one ionic salt, at least one soluble protein, and at least one intermediate energy substrate.

The present invention is also directed to a resuscitation fluid prepared according to the method described above.

These and other aspects of the invention will be understood and become apparent upon review of the specification by those having ordinary skill in the art.

DETAILED DESCRIPTION OF SEVERAL EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The present invention makes a paradigm shift in the design and use of resuscitative fluids. The present resuscitative fluid, discussed in more detail below, is administered to a subject at an ionic strength that is significantly higher than is physiologically normal with the result that it causes transfer of the body's interstitial fluid from the interstitial space into the vascular space to replenish vascular fluid volume. However, the novel fluid is designed to mitigate or avoid the adverse consequences that would normally be expected to accompany such therapy. In addition to an ionic salt, which is present in a hypertonic concentration, the novel fluid also includes an agent designed to help maintain normal aerobic cell metabolism, a soluble protein, at least one intermediate energy substrate, and optionally, an agent to reduce or avoid the body's inflammatory response.

Consequently, the novel resuscitative fluid is administered to a subject in need of such treatment at significantly lower volume than would normally be required and with results that are superior to results normally expected with the use of conventional resuscitative fluids. These results were unexpected due to the beneficial effect on cell metabolism and minimization of inflammatory response that has been demonstrated, while avoiding the adverse consequences one having ordinary skill in the art would expect to accompany the administration of a hypertonic solution.

The ionic salt of the present fluid is preferably a pharmaceutically acceptable salt that ionizes to provide osmotic pressure in an aqueous solution. Preferred salts include sodium chloride (NaCl) and potassium chloride (KCl). NaCl is an especially preferred salt for use as the agent to augment intravascular fluid. In preferred embodiments, the salt is in the form of a saline solution. Those having ordinary skill in the art will recognize that saline is a solution of NaCl in sterile water, used commonly for intravenous infusion.

The concentration of the ionic salt in the present resuscitative fluid is sufficient to cause transfer of fluids from the interstitial space to the vascular space in the body of the subject receiving the fluid. The use of the hypertonic solution causes replenishment of vascular fluid volume by using the subject's own bodily fluids. The ability to utilize the subject's own fluids for cell resuscitation allows treatment using lower volumes of resuscitation fluid than utilized in traditional methods of treating and traditional resuscitation fluids.

Hypertonic saline is highly effective at restoring intravascular volume at modest administered amounts. Hypertonic saline utilizes oncotic forces by the interstitial fluid to resuscitate a subject suffering from shock. Typical hypertonic saline solutions have a concentration of between about 3% and about 7.5%.

In some embodiments, the present resuscitation fluid contains between about 0.9% to about 15% salt by weight of the total solution, more preferably between about 5% to about 10% salt by weight of the total solution. An especially preferred concentration is about 7.5 wt %. It may be preferable to include the salt in the present fluid as a saline solution having a concentration of between about 5% and 10%.

As previously discussed, the use of hypertonic saline alone often results in an inflammatory response in the subject, as well as forcing cell metabolism into an anaerobic regime from which the cells are unable to recover.

The soluble protein component of the present resuscitation fluid acts along with the ionic salt to increase the osmotic pressure in the vascular system of the subject. At least one soluble protein is included in the novel fluid, but two or more types of protein can be used. When it is said that the protein is a "soluble protein", it is meant that the protein is soluble in the hypertonic salt solution of the present fluid at least at the concentration at which it is present in the fluid. The protein is preferably negatively charged, thereby increasing the shift of the chemical potential across the cell membranes and improving the movement of the fluid from the interstitial space to the vascular space, as previously discussed.

The soluble protein is preferably an albumin. Those having ordinary skill in the art will recognize that "albumin" refers generally to any protein with water solubility, which is moderately soluble in concentrated salt solutions, and experiences heat coagulation. Substances containing albumin are called albuminoids. In an exemplary embodiment, the preferred albumin is human serum albumin. Albumin is negatively charged.

In normal mammalian physiology, albumin is necessary for maintaining the osmotic pressure needed for proper distribution of body fluids between the intravascular compartments and body tissues. During episodes of hemorrhagic and/or ischemia disorders, additional albumin may be administered to increase the osmotic pressure as necessary to direct flow of the body's own fluids from the interstitial space to the vascular space.

The soluble protein preferably has antioxidant activity. As used herein, the term "antioxidant activity" refers to substances that slow or prevent the oxidation of other chemicals. The antioxidant activity of the preferred soluble proteins may aid in minimizing reperfusion injury.

In exemplary embodiments, the present resuscitation fluid includes between about 15% and 40% by weight soluble protein, more preferably between about 20% and about 30% by weight soluble protein. An especially preferred concentration is about 25 wt %.

The intermediate energy substrate of the present resuscitation fluid is useful to improve and/or maintain cell metabolism after the cells have been forced into an anaerobic metabolism regime. During periods of hemorrhagic and/or ischemia disorders, the cells are often in an anaerobic environment. Even after oxygen flow is restored to the cells, they are often unable to revert back to aerobic metabolism and ultimately die. The inability to successfully address this metabolic imbalance is a common problem with traditional resuscitation fluids and treatments. The inventors have found that this problem can be overcome by including a suitable intermediate energy substrate in the resuscitation fluid.

Exemplary intermediate energy substrates that are useful in the present invention include keto-acids and their carboxylate anions. Keto-acids are organic acids containing a ketone functional group and a carboxylic acid group. Keto-acids are typically classified as alpha-keto acids, having the keto group adjacent to the carboxylic acid; beta-keto acids, having the ketone group at the second carbon from the carboxylic acid; or gamma-keto acids, having the ketone group at the third carbon from the carboxylic acid.

In an exemplary embodiment, the present intermediate energy substrate is one or more alpha-keto-acid and carboxylate anions thereof. An especially preferred intermediate energy substrate is pyruvate—the carboxylate anion of pyruvic acid. The present intermediate energy substrate is useful for helping cells continue ATP production and for maintaining energy and ionic gradients during periods of ischemia.

In exemplary embodiments, the present resuscitation fluid includes between about 0.1% and about 10% by weight intermediate energy substrate, more preferably between about 0.5% and about 2% by weight intermediate energy substrate. An especially preferred concentration is about 1 wt %.

Optionally, the present fluid contains an agent to reduce or avoid the body's inflammatory response. Typically, this agent acts by aiding cells to mitigate combat intracellular acidosis by scavenging free radicals. As used herein, the terms "agent to reduce or avoid the body's inflammatory response" can be used interchangeably with the terms "agent to mitigate intracellular acidosis".

Acidosis is an increased acidity (i.e., hydrogen ion concentration) of blood plasma. Generally, acidosis is said to occur when arterial pH falls below 7.35. During acidosis, there is an increase in the concentration of free-radicals in the cell environment. An increase in free radicals triggers the body's inflammatory response, resulting in inflammation of the affected area. When the affected area is inflamed, the movement of fluids across the cell membranes is impeded. By inclusion of one or more agents to mitigate intracellular acidosis, the free radicals are scavenged, preventing inflammation. By preventing inflammation, the present resuscitation fluid demonstrates improved rates of flow of fluid from the interstitial space to the vascular space. Although hypertonic saline has been shown to have some anti-inflammatory properties, those properties are not sufficient to combat the increase in free-radicals. Additional free-radical scavenging that is provided by the agent to mitigate intracellular acidosis strengthens the mitigation of cellular acidosis during cellular resuscitation and improves the outcome of the administration of the resuscitative fluid.

In exemplary embodiments, a preferred agent to mitigate intracellular acidosis is N-acetylcysteine. N-acetylcysteine is a free-radical scavenger and is the N-acetyl derivative of the amino acid L-cysteine. In mammals, N-acetylcysteine is a precursor in the formation of antioxidant glutathione in the body.

In exemplary embodiments, the present resuscitation fluid includes between about 0.2% and about 20% by weight of the one or more agents to mitigate intracellular acidosis, more preferably between about 0.5% and about 4% by weight of the agent to mitigate intracellular acidosis. An especially preferred concentration is about 2 wt %.

The resuscitation fluid of the present invention preferably has a pH of between about 6.5 and 7.0, more preferably between about 6.6 and 6.9, even more preferably between about 6.7 and 6.85. In especially preferred embodiments, the present resuscitation fluid has a pH of about 6.8.

In one embodiment, the present resuscitation fluid includes at least one ionic salt, albumin, N-acetylcysteine, and pyruvate. More specifically, in an exemplary embodiment, the present resuscitation fluid includes between about 5% and about 10% of an ionic salt (by weight), between about 0.5% and about 4% N-acetylcysteine (by weight), between about 20% and about 30% albumin (by weight), and between about 0.5% and about 2% pyruvate (by weight).

In another embodiment, the present resuscitation fluid consists essentially of at least one ionic salt, at least one soluble protein, at least one intermediate energy substrate, and at least one agent to mitigate intracellular acidosis.

In yet another embodiment, the present resuscitation fluid consists essentially of NaCl, N-acetylcysteine, albumin, pyruvate, and water.

In one embodiment, the present resuscitation fluid is substantially free of sodium lactate, calcium chloride, and potassium chloride. In yet another embodiment, the present resuscitation fluid is substantially free of sodium lactate. In a different embodiment, the present resuscitation fluid is substantially free of calcium chloride. In an even different embodiment, the present resuscitation fluid is substantially free of potassium chloride. In at least one embodiment, the present resuscitation fluid is substantially free of Ringer's solution or lactated Ringer's solution.

Without being bound to this or any other theory, the inventors believe that the present resuscitation fluid provides resuscitation on a cellular level; by increasing the flow of the body's own fluid from the interstitial space to the vascular space. Traditional resuscitation fluids are unable to achieve this result. Ringer's solution (and similar resuscitation fluids) do not have the osmolarity necessary to mobilize the subject's own fluids. For this reason, larger volumes of fluid are necessary to successfully treat the subject.

Hypertonic saline, alone, results in inflammation of the cell membranes, thereby reducing the flow of fluid from the interstitial space to the vascular space. The present fluid overcomes these problems, as previously discussed, by mitigating the deleterious effects of hypertonic saline, while taking advantage of the beneficial effects provided by the high ionic strength.

In another aspect, the invention is a method of making a resuscitation fluid. The method includes intermixing at least one ionic salt, at least one soluble protein, and at least one intermediate energy substrate component. The method optionally includes intermixing at least one component to mitigate intracellular acidosis.

The intermixing step may be conducted at temperatures below room temperature, at temperatures above room temperature, and/or at a temperature of about room temperature. In some embodiments, it may be desirable to utilize different temperatures at different stages of the intermixing step.

Additionally, the intermixing step may be conducted by one or more of stirring, agitation, heating, and cooling. In some embodiments, it may be desirable to utilize more than one method of intermixing at different stages of the intermixing step.

In some embodiments, the intermixing step may be conducted in a carrier solution, such as those carrier solutions described above. It may be desirable to mix one or more of the components of the resuscitation fluid into a carrier solution individually before combining the components. In additional embodiments, the components may be added to the carrier solution sequentially. In other embodiments, the components may be added to the carrier solution simultaneously, or substantially simultaneously.

It may be desirable to add the components sequentially and slowly to a carrier solution, while maintaining a pH level at or about physiological levels. For example, it may be desirable to add one or more components in a fractional manner, adjusting the pH between additions as needed.

The resuscitation fluid may be supplied in the form of a novel therapeutic composition that is believed to be within the scope of the present invention. The relative amounts of each component in the therapeutic composition may be varied and may be as described above. The resuscitation fluid may be provided in the therapeutic composition so that the preferred amounts of each of the components are supplied by a single dosage form.

When the present combination is supplied along with a pharmaceutically acceptable carrier, a pharmaceutical composition is formed. A pharmaceutical composition of the present invention is directed to a composition suitable for the treatment and/or prevention of one or more of septic shock, hemorrhagic shock, hypotension, acidosis, and hypovolemia. Pharmaceutically acceptable carriers include carrier solutions such as water, saline, phosphate solution or buffer, buffered saline, and other carriers known in the art. Pharmaceutical compositions may also include stabilizers, antioxidants, colorants, anti-microbial agents, bacteriostats, and diluents. Pharmaceutically acceptable carriers and additives are chosen such that side effects from the pharmaceutical composition are minimized and the performance of the composition is not canceled or inhibited to such an extent that treatment is ineffective.

The term "pharmaceutically effective amount" shall mean that amount of a drug of pharmaceutical agent that will elicit the biological or medical response of a tissue, system, animal, or human that is being sought by a researcher or clinician. This amount can be a therapeutically effective amount.

The term "pharmaceutically acceptable" is used herein to mean that the modified noun is appropriate for use in a pharmaceutical product. Pharmaceutically acceptable cations include metallic ions and organic ions. More preferred metallic ions include, but are not limited to, appropriate alkali metal salts, alkaline earth metal salts, and other physiological acceptable metal ions. Exemplary ions include aluminum, calcium, lithium, magnesium, potassium, sodium, and zinc in their usual valences. Preferred organic ions include protonated quaternary ammonium cations, including in part, trimethylamine, diethylamine, N,N'-dibenzylethylenediamine, chloroprocaine, choline, diethanolamine, ethylenediamine, meglumine (N-methylglucamine), and procaine. Exemplary pharmaceutically acceptable acids include without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

In another aspect, the invention is a method of preventing or treating septic shock, hemorrhagic shock, hypotension, acidosis, and/or hypovolemia. The method preferably includes administering to a subject in need of treatment or prevention of one or more of septic shock, hemorrhagic shock, hypotension, acidosis, and/or hypovolemia at least one ionic salt, at least one soluble protein, and at least one intermediate energy substrate component. The method optionally includes administering at least one component to mitigate intracellular acidosis. These components can be administered in the form of a resuscitative fluid.

In the present method, a subject in need of prevention or treatment of shock-related conditions is treated with the previously described resuscitation fluid, wherein the fluid is administered in a dosage or effective amount that is sufficient to constitute a treatment or prevention of shock-related conditions.

As used herein, an "effective amount" means the dose to be administered to a subject and the frequency of administration to the subject which is readily determined by one of ordinary skill in the art, by the use of known techniques and by observing results obtained under analogous circumstances. In determining the effective amount or dose, a number of factors are considered by the attending diagnostician, including, but not limited to, the potency and duration of action of the compounds used; the nature and severity of the condition to be treated as well as on the sex, age, weight, general health, and individual responsiveness of the patient to be treated, and other relevant circumstances.

The phrase "therapeutically-effective" indicates the capability of an agent to prevent, or improve the severity of, the condition, while avoiding adverse side effects typically associated with alternative therapies.

In the present method, the amount of the ionic salt to be used in the novel treatment preferably ranges from about 0.9% to about 15% by weight of the total fluid, the amount of the soluble protein is preferably between about 15% and about 40% by weight of the total composition, and the amount of the intermediate energy substrate is preferably between about 0.1% and about 10% by weight of the total composition. In some embodiments, the novel treatment may further include an amount of between about 0.2% and about 20% by weight of the total composition of at least one agent to help cells combat intracellular acidosis.

In some embodiments, the amount of resuscitation fluid administered according to the present method is between about 5% to about 100% the amount of blood loss, more preferably between about $\frac{1}{8}$th and $\frac{1}{4}$th the total blood loss. Stated differently, for a one liter hemorrhage, the amount of the present resuscitation fluid administered according to the present method would be between about 50 mL to about 1000 mL, more preferably between about 125 mL and about 250 mL.

The amount of novel resuscitation fluid that is used in the subject method may be an amount that, when administered, is sufficient to constitute the prevention or treatment of shock-related conditions. The amount of resuscitation fluid utilized in the present method may vary depending on the severity and/or imminence of the particular shock-related condition in a particular subject.

Dosages can vary within wide limits and will be adjusted to the individual requirements in each particular case. In general, for administration to adults, an appropriate dosage has been described above, although the limits that were identified as being preferred may be exceeded if expedient.

As used herein, the terms "treating" or "to treat" mean to alleviate symptoms, eliminate the causation either on a temporary or permanent basis, or to prevent or slow the appearance of symptoms. The term "treatment" includes alleviation, elimination of causation of or prevention of the conditions described above. Besides being useful for human treatment, the present composition and method are also useful for treatment of mammals, including horses, dogs, cats, rats, mice, sheep, pigs, etc.

The term "subject" for purposes of treatment or prevention includes any human or animal subject who is in need of the prevention of, or treatment for, the above conditions. The subject is typically a human subject.

For methods of prevention, the subject is any human or animal subject, and preferably is a subject that is in need of prevention and/or treatment of the above shock-related conditions. The subject may be a human subject who is at risk for shock, and related conditions, such as those described above. The subject may be at risk due to injury, bleeding, infection, emotional distress, and other known precursors for shock.

The phrases "combination therapy," "co-administration," "administration with," or "co-therapy," in defining the use of the present resuscitation fluid and present method of administering the present resuscitation fluid are intended to embrace administration of each component in a sequential manner in a regime that will provide beneficial effects of the drug combination, and is intended as well to embrace co-administration of these components in a substantially simultaneous manner, such as in a single dosage device having a fixed ratio of these active agents, or in multiple, separate dosage devices for each agent, where the separate dosage devices can be administered together contemporaneously, or administered within a period of time sufficient to receive a beneficial effect from each of the constituent agents of the combination.

The phrases "therapeutically effective" and "effective for the treatment, prevention, or inhibition," are intended to qualify the amount of each component for use in the combination therapy which will achieve the goal of prevention of, or treatment for, shock-related conditions over treatment of each component by itself, while avoiding adverse side effects typically associated with alternative therapies.

Although the combination of the present invention may include administration of each component within an effective time of each respective component, it is preferably to administer each of the respective components contemporaneously, and more preferable to administer the respective components in a single delivery dose.

The present method includes one or more of intravenous, topical, and oral administration. In some embodiments, the components may be admixed before administration. It may be preferred to admix at least two of the components before administration, with the remaining component or components being administered individually to the subject. In another embodiment, each of the components may be administered individually to the subject.

In yet another embodiment, at least one component may be intermixed with a carrier solution, for example, water, before administration to the subject. In some embodiments, it may be desirable to intermix all of the components with a carrier solution before administration to the subject.

The present resuscitation fluid may also be used as a storage solution for organs during organ transplant, for wound irrigation, as a solution for urological and gynecological procedures, to treat intracranial hypertension from head injury, and to help reduce contrast induced nephrotoxicity. Pre-hospital uses for the present resuscitation fluid include ambulance use, battlefield use, emergency room use, trauma, and intensive care use. Similarly, the present resuscitation fluid may be utilized for veterinary use in the same manner it is utilized from human use.

The present resuscitation fluid may be particularly advantageous for use in battlefield, field hospital, and/or ambulatory environments. Prior art resuscitation fluids typically required a dosage rate of about 3 times the amount of blood loss. Stated differently, for every liter of blood loss, a typical prior art resuscitation fluid treatment required 3 liters of resuscitation fluid. As stated above, the present resuscitation fluid is intended to be typically used in dosages less than the total amount of blood loss. Accordingly, the storage and transport of the present resuscitation fluid provides advantages over the prior art resuscitation fluids due to this dosage reduction.

Moreover, in some embodiments, the present resuscitation fluid may be dried, for example by freeze drying or spray drying, to a powder and stored in the powder form. The powdered form of the resuscitation fluid can then be reconstituted with sterile water, saline, or other carrier fluids at the time of administration. The reconstituted resuscitation fluid of the present invention is clear, non-cloudy, stable and ready for use. This ability to store the resuscitation fluid as a powder aids in the shipping and supplying of the resuscitation fluid for use in remote locations, such as battlefields, field hospitals, and third-world countries.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

Example 1

This example illustrates a method of forming an embodiment of the present resuscitation fluid.

To form a 100 mL solution, add to pyrogen free distilled water 7.5 g NaCl (Fisher), 25 g albumin bovine serum (Sigma Aldrich cGMP, ≧98.5%, non-animal source), 2 g N-acetyl cysteine (Sigma, Fraction V, ≧96% heat shock fractionate, remainder mostly globulins), and 1 mL pyruvate (Fluka Chemika, >97% by GC).

Example 2

This example illustrates an additional method of forming an embodiment of the present resuscitation fluid.

50 mL of pyrogen free distilled water were added to a flask on a stir plate. While stirring, 7.5 g NaCl and 2 g N-acetyl cysteine were added to the flask. The pH was adjusted to 7.4 using 1 N NaOH that was sterile filtered (0.2 micron). 1 mL pyruvate was added. After 15 minutes, the pH was adjusted to 7.4 using 1 N NaOH. 20 mL water were added to the flask, followed by the addition of 10 g albumin. The composition was stirred until the albumin was dissolved, then the pH was adjusted to 7.0. An additional 5 g of albumin was added and allowed to dissolve before the pH was adjusted to 7.0. An additional 10 g of albumin was then added and allowed to dissolve while stirring, followed by addition of water to a total volume of 100 mL. The final pH of the fluid was 6.8.

Example 3

This example relates to a rat test, wherein a rat was allowed to hemorrhage without treatment. A 410 g male Sprague Dawley rat was anesthetized with 0.24 mL of 50 mg/mL ketamine, 0.07 mL of 20 mg/mL xylazine, and 0.05 mL of 10 mg/mL acepromazine. The following results were observed:

| Time (s) | Action | MAP (mm Hg) | Notes |
| --- | --- | --- | --- |
| 1130 | Catheters in place | 90 | |
| 1130 | 4 cc hemorrhage | 50 | Initial bleed |
| 1135 | 1.5 cc hemorrhage | 40 | Rebleed |
| 1150 | 1.0 cc hemorrhage | 37 | Rebleed |
| 1225 | 1.0 cc hemorrhage | 45 | |
| 1227 | 1.0 cc hemorrhage | 40 | |
| 1235 | | | death |

Example 4

In Example 4, a rat suffering from hemorrhagic shock was treated with the present resuscitation fluid. A 405 g male Sprague Dawley rate was anesthetized with 0.24 mL of 50 mg/mL ketamine, 0.07 mL of 20 mg/mL xylazine, and 0.05 mL of 10 mg/mL acepromazine. After hemorrhage was induced, the following results were observed:

| Time (s) | Action | MAP (mm Hg) | Notes |
| --- | --- | --- | --- |
| 1423 | Catheters in place | 100 | |
| 1423 | 4 cc hemorrhage | 35 | Initial bleed |
| 1430 | 1 cc hemorrhage | 40 | Rebleed |
| 1436 | 0.5 cc hemorrhage | | Rebleed |
| 1445 | 2 cc hemorrhage | 33 | Rebleed |
| 1450 | 0.2 cc hemorrhage | 36 | Rebleed |
| 1521 | 1 cc resuscitation fluid (Example 2) | 90 | Rat waking up |
| 1525 | Redose anesthesia | 90 | |
| 1536 | No action | 75 | Anesthesia effective |
| 1553 | 1 cc resuscitation fluid (Example 2) | 68 | Rat waking up |
| 1554 | No action | 79 | |
| 1556 | No action | 91 | |
| 1600 | No action | 93 | |
| 1615 | No action | 80 | |
| 1630 | sacrifice | | |

As can be seen from the above data, a rat treated with a small dosage of the present resuscitation fluid (prepared according to the procedure of Example 2) may be successfully resuscitated after significant hemorrhage.

The overall purpose of the experiments in animals is to establish safety, appropriate dosage range, and efficacy prior to evaluation in humans at risk for, or suffering from, shock-related conditions. Since the ultimate purpose of the present compositions and methods is to provide a safe preparation that can be used to treat humans who might not be receiving effective treatment for shock-related conditions, the dosages in the animal studies are modeled after expected dosages for human treatment. Those having ordinary skill in the art will recognize that small animal studies are typically conducted to determine safety, dosage and efficacy prior to treatment in humans. Similarly, those having ordinary skill in the art will recognize that the correlation of rat data to human treatment in this art is well-understood and accepted.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties.

The discussion of the references herein is intended merely to summarize the assertions made by their authors and no admission is made that any reference constitutes prior art. Applicants reserve the right to challenge the accuracy and pertinency of the cited references.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A resuscitation fluid for treating hypovolemia in a subject, the resuscitation fluid consisting of:
    an ionic salt at a salt concentration between about 0.9% and about 15% by weight of the resuscitation fluid;
    a soluble protein at a protein concentration between about 15% and about 40% by weight of the resuscitation fluid, wherein the soluble protein is albumin;
    an intermediate energy substrate at an energy substrate concentration between about 0.1% and about 10% by weight of the resuscitation fluid;
    an agent to mitigate intracellular acidosis at an agent concentration between about 0.2% and about 20% by weight of the resuscitation fluid,
    a buffer, and
    water, wherein the resuscitation fluid has a pH adjusted by the buffer to be between about 6.5 and about 7.0.

2. The resuscitation fluid according to claim 1, wherein the ionic salt has a salt concentration between about 5% and about 10% by weight of the resuscitation fluid.

3. The resuscitation fluid according to claim 1, wherein the protein concentration is between about 20% and about 30% by weight of the resuscitation fluid.

4. The resuscitation fluid according to claim 1, wherein the energy substrate concentration is between about 0.5% and about 2% by weight of the resuscitation fluid.

5. The resuscitation fluid according to claim 1, wherein the agent concentration is between about 0.5% and about 4% by weight of the resuscitation fluid.

6. The resuscitation fluid according to claim 1, wherein the agent to mitigate intracellular acidosis is N-acetylcysteine.

7. The resuscitation fluid according to claim 1, wherein the soluble protein is human serum albumin.

8. The resuscitation fluid according to claim 1, wherein the intermediate energy substrate is a keto-acid containing a ketone functional group and a carboxylic acid group.

9. The resuscitation fluid according to claim 1, wherein the intermediate energy substrate is a carboxylate anion of a keto-acid containing a ketone functional group and a carboxylic acid group.

10. The resuscitation fluid according to claim 1, wherein the intermediate energy substrate is pyruvate.

11. A resuscitation fluid for treating hypovolemia in a subject, the resuscitation fluid consisting of
an ionic salt;
a soluble protein, wherein the soluble protein is albumin;
an intermediate energy substrate, wherein the intermediate energy substrate is pyruvate;
an agent to mitigate intracellular acidosis, wherein the agent to mitigate intracellular acidosis is N-acetylcysteine,
a buffer, and
water, wherein the resuscitation fluid has a pH adjusted by the buffer to be between about 6.5 and about 7.0.

12. The resuscitation fluid according to claim 11, wherein the resuscitation fluid consists of the ionic salt between about 0.9% and about 15% by weight; albumin between about 15% and about 40% by weight; pyruvate between about 0.1% and about 10% by weight; and N-acetylcysteine between about 0.2% and about 20% by weight.

13. The resuscitation fluid according to claim 11, wherein the ionic salt is sodium chloride.

14. The resuscitation fluid according to claim 11, wherein the soluble protein is human serum albumin.

15. A resuscitation fluid for treating hypovolemia in a subject, the resuscitation fluid consisting of sodium chloride; albumin; pyruvate; N-acetylcysteine, a buffer, and water, wherein the resuscitation fluid has a pH adjusted by the buffer to be between about 6.5 and about 7.0.

16. The resuscitation fluid according to claim 15 consisting of sodium chloride between about 0.9% and about 15% by weight; albumin between about 15% and about 40% by weight; pyruvate between about 0.1% and about 10% by weight; and N-acetylcysteine between about 0.2% and about 20% by weight.

17. The resuscitation fluid according to claim 15 consisting of sodium chloride between about 5% and about 10% by weight; albumin between about 20% and about 30% by weight; pyruvate between about 0.5% and about 2% by weight; and N-acetylcysteine between about 0.5% and about 4% by weight.

18. A method of treating hypovolemia, the method comprising:
administering to a subject in need of treatment of hypovolemia a resuscitation fluid comprising an ionic salt, a soluble protein, an intermediate energy substrate, an agent to mitigate intracellular acidosis, and water, wherein the resuscitation fluid is a solution.

19. The method according to claim 18 further comprising intermixing the ionic salt, the soluble protein, the intermediate energy substrate, and the agent to mitigate intracellular acidosis to form the resuscitation fluid before administering the resuscitation fluid to the subject.

20. The method according to claim 18, wherein the administration is one or more of intravenous, topical, and oral.

21. The method according to claim 18, wherein the resuscitation fluid comprises the ionic salt between about 0.9% and about 15% by weight; the soluble protein between about 15% and about 40% by weight; the intermediate energy substrate between about 0.1% and about 10% by weight; and the agent to mitigate intracellular acidosis between about 0.2% and about 20% by weight.

22. The method according to claim 21, wherein the resuscitation fluid comprises the ionic salt between about 5% and about 10% by weight of the resuscitation fluid.

23. The method according to claim 21, wherein the resuscitation fluid comprises the soluble protein between about 20% and about 30% by weight of the resuscitation fluid.

24. The method according to claim 21, wherein the resuscitation fluid comprises the intermediate energy substrate between about 0.5% and about 2% by weight of the resuscitation fluid.

25. The method according to claim 21, wherein the resuscitation fluid comprises the agent to mitigate intracellular acidosis between about 0.5% and about 4% by weight of the resuscitation fluid.

26. The method according to claim 18, wherein the agent to mitigate intracellular acidosis comprises N-acetylcysteine.

27. The method according to claim 18, wherein the soluble protein comprises albumin.

28. The method according to claim 27, wherein the soluble protein comprises human serum albumin.

29. The method according to claim 18, wherein the intermediate energy substrate comprises pyruvate.

30. The method according to claim 18, wherein the resuscitation fluid further comprises a buffer.

31. The method according to claim 30, wherein the resuscitation fluid has a pH between about 6.5 and about 7.0.

32. The method according to claim 18, wherein the resuscitation fluid consists essentially of the ionic salt between about 0.9% and about 15% by weight; the soluble protein between about 15% and about 40% by weight; the intermediate energy substrate between about 0.1% and about 10% by weight; the agent to mitigate intracellular acidosis between about 0.2% and about 20% by weight; and water, wherein the resuscitation fluid has a pH adjusted by a buffer to be between about 6.5 and about 7.0.

33. The method according to claim 32, wherein the resuscitation fluid consists essentially of the ionic salt between about 5% and about 10% by weight.

34. The method according to claim 18, wherein the resuscitation fluid consists essentially of the ionic salt between about 5% and about 10% by weight; the soluble protein between about 20% and about 30% by weight; the intermediate energy substrate between about 0.5% and about 2% by weight; the agent to mitigate intracellular acidosis between about 0.5% and about 4% by weight; and water, wherein the resuscitation fluid has a pH adjusted by a buffer to be between about 6.5 and about 7.0.

35. The method according to claim 18, wherein the resuscitation fluid consists essentially of sodium chloride between about 0.9% and about 15% by weight; albumin between about 15% and about 40% by weight; pyruvate between about 0.1% and about 10% by weight; N-acetylcysteine between about 0.2% and about 20% by weight; and water, wherein the resuscitation fluid has a pH adjusted by a buffer to be between about 6.5 and about 7.0.

36. The method according to claim 18, wherein the resuscitation fluid consists essentially of sodium chloride between about 5% and about 10% by weight; albumin between about 20% and about 30% by weight; pyruvate between about 0.5% and about 2% by weight; N-acetylcysteine between about 0.5% and about 4% by weight; and water, wherein the resuscitation fluid has a pH adjusted by a buffer to be between about 6.5 and about 7.0.

37. A method of treating hypovolemia, the method comprising:
administering to a subject in need of treatment of hypovolemia the resuscitation fluid of claim 1.

38. A method of treating hypovolemia, the method comprising:
administering to a subject in need of treatment of hypovolemia the resuscitation fluid of claim 11.

39. A method of treating hypovolemia, the method comprising:
administering to a subject in need of treatment of hypovolemia the resuscitation fluid of claim 15.

40. The resuscitation fluid according to claim 11, wherein the resuscitation fluid consists of the ionic salt between about 5% and about 10% by weight; albumin between about 20% and about 30% by weight; pyruvate between about 0.5% and about 2% by weight; and N-acetylcysteine between about 0.5% and about 4% by weight.

41. A method of treating a hypovolemic subject suffering from a certain amount of blood loss, the method comprising:
administering to the hypovolemic subject a resuscitation fluid in a treatment amount that is less than three times the certain amount of blood loss, wherein the resuscitation fluid comprises an ionic salt, a soluble protein, an intermediate energy substrate, an agent to mitigate intracellular acidosis, and water, wherein the resuscitation fluid is a solution.

42. The method as in claim 41, wherein the treatment amount is less than the certain amount of blood loss.

* * * * *